(12) United States Patent
Ya et al.

(10) Patent No.: US 8,586,106 B2
(45) Date of Patent: Nov. 19, 2013

(54) FATIGUE-RELIEVING HERBAL EXTRACTS AND BEVERAGES COMPRISING THE SAME

(75) Inventors: Cai Ya, Shanghai (CN); Jian JiangBo, Shanghai (CN); Liu Weichang, Shangai (CN); Peng XiaoYun, Shanghai (CN); Zou MinLiang, Shanghai (CN)

(73) Assignee: The Concentrate Manufacturing Company of Ireland (BM)

( * ) Notice: Subject to any disclaimer, the term of this patent is extended or adjusted under 35 U.S.C. 154(b) by 0 days.

(21) Appl. No.: 13/311,833

(22) Filed: Dec. 6, 2011

(65) Prior Publication Data

US 2013/0142891 A1    Jun. 6, 2013

(51) Int. Cl.
*A61K 36/00* (2006.01)
*A61K 36/254* (2006.01)
*A61K 36/815* (2006.01)

(52) U.S. Cl.
USPC .......................................... 424/725; 424/728

(58) Field of Classification Search
None
See application file for complete search history.

(56) References Cited

U.S. PATENT DOCUMENTS

| | | | |
|---|---|---|---|
| 7,122,382 | B1 | 10/2006 | Hayashizaki |
| 7,300,676 | B2 | 11/2007 | Chen |
| 2009/0310839 | A1 | 12/2009 | Katzenelson |
| 2010/0009052 | A1 * | 1/2010 | Canessa et al. ............... 426/319 |
| 2010/0080821 | A1 * | 4/2010 | Spiegel ................... 424/195.15 |
| 2010/0285147 | A1 | 11/2010 | Motoune |

FOREIGN PATENT DOCUMENTS

| | | |
|---|---|---|
| CN | 1047089 | 11/1990 |
| CN | 1088451 | 6/1994 |
| CN | 1131028 | 9/1996 |
| CN | 1663607 | 9/2005 |
| CN | 101032548 A * | 9/2007 |
| CN | 101115493 | 1/2008 |
| CN | 101396118 | 4/2009 |
| CN | 101884774 | 11/2010 |
| CN | 101986879 | 3/2011 |
| JP | 2003061613 | 3/2003 |
| JP | 2005035999 A * | 2/2005 |
| KR | 20050001730 | 1/2005 |
| KR | 20050021825 | 3/2005 |
| KR | 20070111623 | 11/2007 |
| KR | 20070111624 | 11/2007 |
| KR | 20070118754 | 12/2007 |
| KR | 100849244 | 7/2008 |
| KR | 2010083939 A * | 7/2010 |

OTHER PUBLICATIONS

Kwon, et al., "Induction of Quinone Reductase, an Anticarcinogenic Marker Enzyme, by Medicinal Herb Extracts", Nutraceuticals and Food, vol. 7, No. 4, Dec. 2002, pp. 358-366.

* cited by examiner

*Primary Examiner* — Qiuwen Mi
(74) *Attorney, Agent, or Firm* — Banner & Witcoff, Ltd.

(57) ABSTRACT

Herbal extracts are described. The extracts are prepared from combinations of herb parts. The extracts, and beverage products containing the extracts, provide the consumer with a perception of increased energy.

8 Claims, 7 Drawing Sheets

Fig. 1. Relieving physical Fatigue Efficacy Data– Burden Swimming

Fig. 2. Relieving physical Fatigue Efficacy Data— Blood Lactic Acid

Fig. 3. Relieving physical Fatigue Efficacy Data— Serum Urea

Fig. 4. Relieving physical Fatigue Efficacy Data— Glycogen

Fig. 6. Perceived Energy Boost– Sustained energy increase

Fig. 7

FATIGUE-RELIEVING HERBAL EXTRACTS AND BEVERAGES COMPRISING THE SAME

FIELD OF THE INVENTION

The invention relates to herbal extracts, methods of preparing herbal extracts and beverages containing the herbal extracts. The herbal extracts and beverages provide a perceivable fatigue-relieving benefit.

BACKGROUND

Consuming beverages to relieve fatigue has long been known in the art. Coffee beverages are consumed throughout the world for stimulatory effects. Yerba maté is a beverage common in South America where it is consumed for its stimulatory effects. Yerba maté is made from the stems and leaves of *Ilex paraguarensis*, a member of the Holly family, Aquifoliaceae. The mate beverage is usually prepared by one or more additions of boiling water to the dried plant material. The repeated additions of boiled water extract the stimulants from the plant.

Caffeine is considered the principal stimulant in Yerba maté and in coffee beverages. However, excessive consumption of caffeine can give rise to undesirable side effects, such as palpitations, nausea, urinary dysfunction and visual disturbances.

Traditional Chinese medicine (TCM) is gaining increasing attention in the West. For example. *Ephedra*, an extract of the plant *Ephedra sinica*, also known as ma huang has been used as a dietary supplement for treating asthma and hay fever. Ginseng is an additional example of an herbal extract found in supplements and foodstuffs in the West. In some cases, however, the stimulants may have unhealthful effects. In particular, *Ephedra* use has been associated with serious side effects and, in some cases, death. The Food and Drug Administration banned the sale of ephedra in 2006.

Accordingly, there remains a need in the art for beverages that provide an energy-enhancing stimulatory effect but do not require high caffeine levels.

SUMMARY

In an aspect, an herbal extract composition comprising herbal extracts of Duan-Geng-Wu-Jia, Gou-Qi-Zi and Huang-Jing is provided. The extracts are present in the composition according to the following formulae:

$$\frac{1}{5} \leq \frac{B}{C} \leq 5,$$

and $$\frac{1}{5} \leq \frac{A}{B+C} \leq 5;$$

wherein A, B, and C are Duan-Geng-Wu-Jia, Gou-Qi-Zi, and Huang-Jing, respectively, and wherein the amounts of A, B, and C are w/w/w.

In another aspect, a method of preparing an herbal extract composition is provided. The method comprises steps of combining a Duan-Geng-Wu-Jia herb part, a Gou-Qi-Zi herb part and a Huang-Jing herb part. The parts are combined in accordance with the formulae:

$$\frac{1}{5} \leq \frac{B}{C} \leq 5,$$

and $$\frac{1}{5} \leq \frac{A}{B+C} \leq 5,$$

wherein A, B, and C are Duan-Geng-Wu-Jia, Gou-Qi-Zi, and Huang-Jing, respectively, and wherein A, B, and C are present in a w/w/w basis. The combined herb parts are heated in water to obtain an extraction liquid. The extraction liquid is concentrated to provide an herbal extract composition.

In still another aspect, a method of preparing an herbal extract composition is provided. The method comprises steps of heating separately each of a Duan-Geng-Wu-Jia herb part, a Gou-Qi-Zi herb part and a Huang-Jing herb part. The herb parts are heated separately in water to obtain extraction liquids. The extraction liquids are concentrated separately to provide a Duan-Geng-Wu-Jia herb extract, a Gou-Qi-Zi herb extract and a Huang-Jing herb extract. The herb extracts are combined in accordance with the formulae:

$$\frac{1}{5} \leq \frac{B}{C} \leq 5,$$

and $$\frac{1}{5} \leq \frac{A}{B+C} \leq 5,$$

wherein A, B, and C are Duan-Geng-Wu-Jia, Gou-Qi-Zi, and Huang-Jing, respectively, and wherein A, B, and C are present in a w/w/w basis.

In yet another aspect, a beverage product is provided. The beverage product comprises an herbal extract composition. The herbal extract composition comprises about 26.5 to 239 mg/L saponins, about 126 to 1134 mg/L flavonoids, about 26 to 235 mg/L amino acids, and about 335 to 3015 mg/L polysaccharides.

DETAILED DESCRIPTION

Aspects of the present invention relate to herbal extracts providing enhanced performance to consumers. The herbal extracts may be delivered to the consumer in beverage products and find particularly use in alleviating fatigue and enhancing sports performance.

Herbal Extracts Used in the Beverage Products

In some aspects, an herbal extract composition is provided. The herbal extract may be prepared from extracting components from herb parts. In one aspect, a composition comprises extracts from a combination of several herbs. For example, the combination may include Duan-Geng-Wu-Jia. also named Wu-Geng-Wu-Jia (*Acanthopanax sessiliflorus* (Rupr. Et Maxim.) Seem., or *Eleutherococcus sessiliflorus* (Rupr. et Maxim.) S. Y. Hu), Gou-Qi-Zi (the fruit from herbs of *Lycium barbarum* L. (also known as *L. halimifolium* Mill.), *Lycium chinense* Mill, *Lycium dasystemum* Pojark, *Lycium chinense* Mill. var *potaninii* (Pojark.) A. M. Lu) and Huang-Jing (Rhizoma Polygonati Sibirici, Rhizoma Polygonati Cyrtonematis, Rhizoma Polygonati Kingiani).

Duan-Geng-Wu-Jia, like Ginseng (Radix Ginseng), American Ginseng (*Radix Panacis Quinquefolii*) and Ci-Wu-Jia (*Radix et Rhizoma Acanthopanacis Senticosi*), belongs to the family of Araliaceae, and Ci-Wu-Jia is in the same genus as Duan-Geng-Wu-Jia.

Duan-Geng-Wu-Jia, approved by the Chinese Ministry of Health as a New Resource Food in 2008, has long been consumed in Northeast China, Korea and Japan as a food. Duan-Geng-Wu-Jia active ingredients are known to include saponins, flavonoids, amino acids and polysaccharides. The leaf, stem and fruit are edible. Typically, Duan-Geng-Wu-Jia leaf and stem contain higher saponins and flavonoids than the fruit.

Based on Traditional Chinese Medicine theory, Ginseng, American Ginseng, and Ci-Wu-Jia benefit "Qi," a TCM term relating to mental and physical energy. In China, Ginseng, American Ginseng, and Ci-Wu-Jia, are widely used as raw materials of medicines or healthy foods for Qi benefit. However, pursuant to the Chinese Ministry of Health, they are not used in general foods.

The root bark of Duan-Geng-Wu-Jia is used in one traditional medicine "Wu-Jia-Pi wine" to treat rheumatism and arthralgia. Duan-Geng-Wu-Jia stem and leaf are consumed as a vegetable. Duan-Geng-Wu-Jia fruit is recorded in traditional Chinese medicine theory as benefiting "kidney" and "liver" function and strengthen bone and muscle.

In some embodiments, Gou-Qi-Zi, also known as Goji, wolfberry, or Goji-berry, is well-known by its "Yin" benefit, in traditional Chinese medicine theory. The "Pharmacopoeia of the People's Republic of China" suggests Goji berry for using in treatment of "kidney disorders" impotence and nocturnal emission, dizziness and tinnitus, wasting-thirst caused by "inner heat," hypochromic anemia (also referred to as chlorosis caused by "blood deficiency"), and poor eyesight. Goji-berry is also used as general food. Goji berry is already known for its multiple health benefits, based on its multi-nutrients (e.g. zeaxanthin, vitamins, and polysaccharides) composition.

Huang-Jing belongs to the Lily family. Three species of the Lily family regarded as authentic Huang-Jing and approved in the "Pharmacopoeia of the People's Republic of China" are Rhizoma Polygonati Sibirici, Rhizoma Polygonati Cyrtonematis, and Rhizoma Polygonati Kingiani. Huang-Jing extracts may be used as medicine or consumed as general foods freshly, dried, or processed by steam or boiled water, sometimes stewed and/or steamed by Chinese wine. As recorded in Traditional Chinese Medicine theory, Huang-Jing enhances "Yin," benefiting the "kidney," the "spleen," and enhances "lung" moisture for dry cough less sputum due to Yin-deficiency with "lung" dryness, and hemoptysis and hectic fever. As published in "Pharmacopoeia of the People's Republic of China," Huang-Jing is used as medicine to benefit "Qi" deficiency in the spleen and stomach, which manifests as poor appetite, hypodynamia, and a dry and wasting-thirst caused by "inner heat" (wasting thirst may also be referred to as diabetes). Other traditional indications are as a supplement in cases of joint weakness, and for the treatment of prematurely graying hair.

In some aspects, the Duan-Geng-Wu-Jia herb part used is one or more of leaf, stem, root bark, stem bark, fruit, and/or flower. In particular aspects, only the leaf, stem, and fruit of Duan-Geng-Wu-Jia are used as the Duan-Geng-Wu-Jia herb part. In some aspects, the part of Gou-Qi-Zi used is the dried fruit berry. In some aspects, the Huang-Jing part used is the dried rhizome.

The herb parts may be combined in particular ratios before extraction to provide an extract that confers a fatigue relieving benefit to the consumer. In other aspects, the herb extracts may be prepared separately then combined. Preparing the extract using the combinations of the herbs in particular amounts provides the fatigue-relieving effect. In a particular embodiment, the Duan-Geng-Wu-Jia, Gou-Qi-Zi and Huang-Jing parts are combined, prior to extraction, according to the following formulae:

$$\frac{1}{5} \le \frac{B}{C} \le 5$$

$$\frac{1}{5} \le \frac{A}{B+C} \le 5,$$

wherein A, B, and C are Duan-Geng-Wu-Jia, Gou-Qi-Zi, and Huang-Jing, respectively, and wherein the ratios of A, B, and C are on a w/w/w basis. The Duan-Geng-Wu-Jia amount represents the total weight of all parts of the herb used to make the extract.

In some aspects, the parts may be combined according to the following formulae:

$$\frac{2}{3} \le \frac{B}{C} \le \frac{3}{2}$$

$$\frac{1}{3} \le \frac{A}{B+C} \le 1.$$

In other aspects, B/C=1, and A/(B+C)=0.75, on a w/w/w basis.

In some aspects the herbal extract may be consumed by a consumer in a beverage product. In some aspects, the beverage products containing the herbal extract may contain saponins (calculated as ginsengoside Re) ranging from about 20 mg/L to about 250 mg/L (for example, from 26.5 to 239 mg/L); total flavonoids content (calculated as rutin) about 100 mg/L to about 1200 mg/L (for example, from 126 to 1134 mg/L); total free amino acids content ranging from about 20 mg/L to about 250 mg/L (for example, from 26 to 235 mg/L) and total polysaccharides content ranging from about 300 mg/L to about 3300 mg/L (for example from 335 to 3015 mg/L). As used herein, "about" means plus or minus 10% of the indicated value.

The Brix level of a final beverage may be in a range from 0.2 to 18.0; for example, the range may be between 0.2 and 1.0, between 1.0 and 5.0, between 5.0 and 10.0, between 10.0-and 15.0, or between 15.0 and 18.0.

Effects of the Herbal Extract

The herbal extracts provide a perceived reduction in fatigue. Without wishing to be bound by a particularly mechanism it is thought that the herbal extracts contain one or more ingredients that affect physiology, including saponins, flavonoids, polysaccharides and free amino acids.

Experiments were performed to determine the physiological effects of the herbal extracts. The amount of time-to-exhaustion while burden swimming is a useful objective measure for determining fatigue. As Example 3 demonstrates, the herbal extracts disclosed herein provide a measureable increase in the time taken for mice to become exhausted during a burden swimming process, indicating that the herbal extracts can extend endurance and reduce fatigue.

To further characterize the effects of the herbal extract, biochemical analyses of metabolites were performed. Accumulation of metabolites during exertion is a key reason for fatigue. Lactic acid and hydrogen ions are key important factors. Lactic acid is produced as a metabolite during glycolysis in hypoxic condition. As lactic acid increases, the dissociated hydrogen ions lead to a decrease of pH value in muscle cells. The pH decrease reduces the activity of enzymes involved in glycolysis, resulting in decreased muscle strength. Elevating the blood lactic acid clearance rate, or lowering the production of blood lactic acid, speeds up the alleviation of fatigue and physical recovery from exertion. As Example 4 shows, blood lactic acid in response to exercise was decreased in mice consuming the herbal extract. Thus, the herbal extract may contribute to reducing fatigue and enhancing stamina by reducing lactic acid levels.

Serum urea levels can increase during exercise as a result of increased catabolism of protein and nitrogen compounds enhanced. Increased serum urea indicates that the body has a reduced ability to adapt during load exercise. As Example 5 shows, mice that consumed the herbal extract had a lower content of serum urea, indicating that the herbal extracts provide sustained endurance before the body begins to catabolize protein. In addition, these data support the hypothesis that consuming the herbal extract may enhance the ability of the consumer to adapt under severe load.

Glucose is a key energy resource for muscle, as well as for the function of central nervous system. Glycogen contains glucose in a stored form and releases glucose to supply energy during exercise. When glycogen supplies are used up, muscle ability decreases and exercise-induced fatigue results. Example 6 shows that glycogen stores are higher in mice consuming the herbal extract. These data indicate that one mechanism underlying reduced fatigue and extended ability to exercise may be elevated glycogen storage.

A positive result in time-to-exhaustion test and in any two of three biological studies (blood lactic acid, serum urea and glycogen) is recognized by academia and the Chinese Ministry of Health as sufficient to certify efficacy in relieving physical fatigue. See, for example, references 2 and 3. Mice who consumed the herbal extract showed extended time-to-exhaustion, reduced blood lactic acid, reduced serum urea, and elevated glycogen. Collectively, these studies establish that the herbal extract can confer relief from physical fatigue and enhance endurance. See references 1-4

Data in human studies further support a perceived effect on fatigue relief. All the beverages containing the herbal extract resulted in a perceived energy boost. See FIG. 5 and Example 7. Notably, the caffeine-free beverage (FIG. 5; "237") was particularly effective. After 30 minutes more test participants perceived an energy boost than any of the other beverages, including the control caffeine beverage (FIG. 5; "Caffeine Control"). The data from 40 min to 60 min also shows that, in addition to faster onset, the caffeine-free beverage gave a perceived energy boost in a greater percentage of the test population than the other beverages. Thus, in some aspects, a beverage product causes a perception of increased energy in at least 80% of consumers within an hour of consumption.

An extended time course of the perceived effects was performed. See FIG. 6. The data establish that an effect is perceived for the beverages for over 4 hours after consumption. Again, the caffeine-free herbal extract beverage was particularly effective. Up until 150 minutes after consumption the caffeine-free beverage (FIG. 6; "237") showed perceived energy in a greater percentage of the test population than the other beverages.

Synergy Effect Evaluation

The "Probability Sum" was used to evaluate the synergistic effects of drug combinations, by calculating the Q value according to Jin's formula (See Reference 5-7):

$$Q \text{ Value: } Q = E_{A+B}/(E_A + E_B - E_A * E_B)$$

Wherein,

E: Rate of Effect;

$$E_A = (T_A - T_C)/T_C$$

$$E_B = (T_B - T_C)/T_C$$

$$E_{A+B} = (T_{A+B} - T_C)/T_C$$

$E_A$: the rate of effect of drug-A; $T_A$: the effect of drug A;
$E_B$: the rate of effect of drug-B; $T_B$: the effect of drug B;
$E_{A+B}$: the rate of effect of combination drug of A plus B; $T_{A+B}$: the effect of combination drug of A plus B.

TABLE 1

Correspondence of Q value to effect.

| Q value | Level of Synergistic Effect |
|---|---|
| <0.55 | Significant Antagonism |
| 0.55~0.85 | Antagonism |
| 0.85~1.15 | Additive |
| 1.15~20 | Synergism |
| >20 | Significant Synergism |

Three herbal extract combinations were tested to study the synergistic effect between Duan-Geng-Wu-Jia and the Gou-Qi-Zi/Huang-Jing mixture. Duan-Geng-Wu-Jia extract alone (calculated as human dose of 0.2 gram/60 kg/day; "Drug A"); Huang-Jing extract plus Gou-Qi-Zi herb extract (0.4 gram/60 kg/day; "Drug B"), and Duan-Geng-Wu-Jia, Huang-Jing and Gou-Qi-Zi combined "0.6 gram/60 kg/day; Drug A+B." The weight ratio between Huang-Jing and Gou-Qi-Zi was one.

Fifty-Eight male mice were randomly separated into 4 groups: control group (17 mice), group of "Duan-Geng-Wu-Jia, Huang-Jing, and Gou-Qi-Zi" (17 mice), group "Duan-Geng-Wu-Jia" (12 mice), and group "Huang-Jing combined with Gou-Qi-Zi" (12 mice). 3 groups were fed with the herb extract for 30 days. The control group water contained no extract.

The amount of time-to-exhaustion while burden swimming is a useful objective measure determining fatigue. A Q value of 4.30 was calculated, based on the test results. This value indicates a synergistic effect between Duan-Guang-Wu-Jia and Gou-Qi-Zi/Huang-Jing mix was observed, indicating the novelty of this herbal recipe combination.

TABLE 2

Swimming Time and Q value calculation.

| Groups | Dose (g/60kg/day) | Forced swimming time (seconds, Average ± Standard Deviation) |
|---|---|---|
| Control | 0 | 754.6 ± 541.5 |
| Duan-Geng-Wu-Jia | 0.2 | 617.2 ± 184.4 |
| Huang-Jing and Gou-Qi-Zi | 0.4 | 915.6 ± 658.3 |
| Duan-Geng-Wu-Jia, Huang-Jing, and Gou-Qi-Zi | 0.6 | 982.4 ± 692.6 |

$$Q = E_{A+B} / (E_A + E_B - E_A * E_B)$$

$$= [(T_{A+B} - T_{control})/T_{control}] / \{[(T_A - T_{control})/T_{control}] +$$

$$[(T_B - T_{control})/T_{control}] -$$

$$[(T_A - T_{control})/T_{control}] * [(T_B - T_{control})/T_{control}]$$

$$= [(982.4 - 754.6)/754.6] / \{[(617.2 - 754.6)/754.6] +$$

$$[(915.6 - 754.6)/754.6] -$$

$$[(617.2 - 754.6)/754.6] * [(915.6 - 754.6)/754.6]$$

$$= 4.30$$

Preparation of the Herbal Extract

Figure 7:
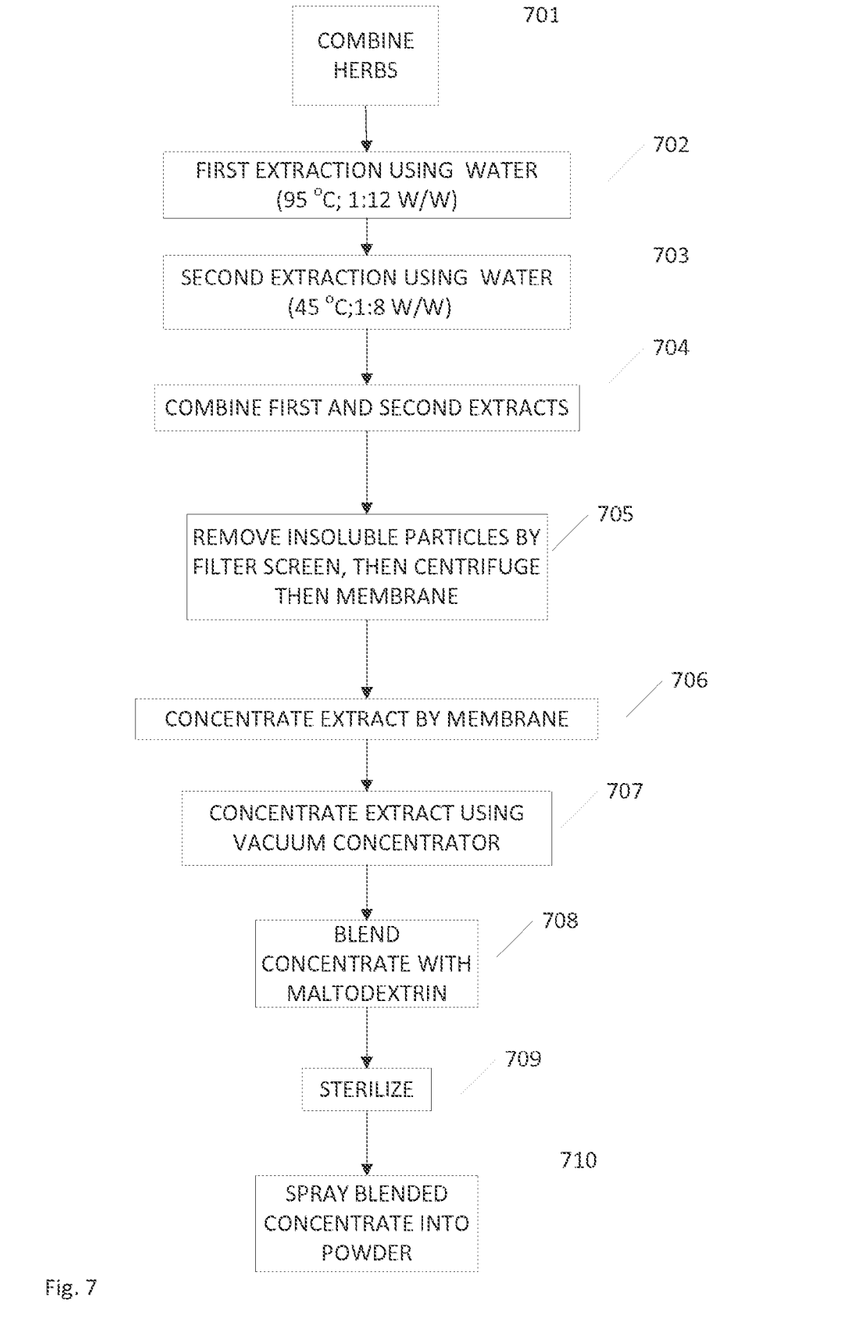
FIG. 7 illustrates a method of preparing an herbal extract.

The herbal extract may be prepared in accordance with the steps shown in FIG. 7. In a first step, 701, the herbs are added to an extraction tank. For example, in 200 Kg of herb materials, there may be 71.4 Kg Duan-Geng-Wu-Jia leaves, 14.3 Kg Duan-Geng-Wu-Jia fruit, 57.1 Kg Gou-Qi-Zi and 57.1 Kg Huang Jing. In step 702 a first extract may be obtained by adding warm water (e.g., 95° C.) to the herbs at a ratio of about 1:12 w/w. The water extract is removed from the extract tank. In step 703, a second extraction may be performed using cooler water (e.g. 45° C.) at a ratio of 1:8 w/w. The first and second extracts may then be combined (Step 704). If undesirable particulate matter is present in the extract it may be removed in step 705 in a three-part process using a filter screen. In a first part, the extract may be poured through a filter screen. In a second part, the resulting filtrate may be centrifuged to remove additional insoluble material. In a third part, the supernatant may be pressed through a membrane with small pores to provide a liquid extract substantially free of particulate matter. In some aspects, only one or two of the three part process may be used to obtain the extract substantially free of particulate matter.

In steps 706 and 707 the extraction liquid may be concentrated. In some aspects, concentration may be achieved in a two-step process. In a first step 706, membrane may be used to concentrate the liquid. In a second step 707, a vacuum concentrator may be used to remove liquid and provide a concentrate.

The concentrate may then be blended with additives (step 708; e.g. with maltodextrin), sterilized using ultra-high temperature processing (step 709) and then sprayed into a powder for further use or storage (step 710). The table below shows a typical chemical content in herbal extract, the herbal extracts used in other examples possess the same or similar chemical content.

The chemical profile of herbal extracts may vary slightly due to the herbal source, extraction solvent and additives such as maltodextran, which is added to facilitate the drying process. A typical extract contains ingredients and amounts as shown below.

TABLE 3

Percentage of Ingredients in an Exemplary Spray-dried Herbal Extract Powder

| Ingredients | (weight %) |
|---|---|
| Saponins (calculated as ginsengoside Re) | 0.990 |
| Flavonoids (calculated as rutin) | 4.700 |
| Polysaccharides | 12.500 |
| Total Free Amino Acid | 0.973 |

In other aspects, extracts of the herbs can be prepared individually then later recombined to arrive at the combined herbal extract.

It should be understood that beverages and other beverage products in accordance with this disclosure may have any of numerous different specific formulations or constitutions. The formulation of a beverage product in accordance with this disclosure can vary to a certain extent, depending upon such factors as the product's intended market segment, its desired nutritional characteristics, flavor profile and the like. For example, it will generally be an option to add further ingredients, to the formulation of a particular beverage embodiment, including any of the beverage formulations described below. Additional (i.e., more and/or other) sweeteners may be added, flavorings, electrolytes, vitamins, fruit juices or other fruit products, colorants, tastants, masking agents and the like, flavor enhancers, and/or carbonation typically can be added to any such formulations to vary the taste, mouthfeel, nutritional characteristics, etc.

In certain embodiments of the beverage and other products disclosed here, color derived from one or more natural sources may be added. The color derived from one or more natural sources may be selected from the group consisting of purple sweet potato, black carrot, purple corn, red beet, carthamus yellow, gardenia blue, and combinations thereof. The at least one color derived from natural sources may be present in the beverage product at a concentration of between 150 and 500 ppm. In certain embodiments, ascorbic acid is also present in the beverage product.

In general, a beverage in accordance with this disclosure typically comprises at least water, one or more colors derived from natural sources, acidulant and flavoring, and typically also sweetener. Exemplary flavorings which may be suitable for at least certain formulations in accordance with this disclosure include herbal flavoring, fruit flavoring, spice flavorings and others. Carbonation in the form of carbon dioxide may be added for effervescence. Preservatives can be added if desired, depending upon the other ingredients, production technique, desired shelf life, etc. Additional and alternative suitable ingredients will be recognized by those skilled in the art given the benefit of this disclosure.

The beverage products disclosed here include beverages, i.e., ready to drink liquid formulations, beverage concentrates and the like. Beverages include, e.g., enhanced waters, liquid, slurry or solid concentrates, fruit juice-flavored and juice-containing beverages.

At least certain exemplary embodiments of the beverage concentrates contemplated are prepared with an initial volume of water to which the additional ingredients are added. Full strength beverage compositions can be formed from the beverage concentrate by adding further volumes of water to the concentrate. Typically, for example, full strength beverages can be prepared from the concentrates by combining approximately 1 part concentrate with between approximately 3 to approximately 7 parts water. In certain exemplary embodiments the full strength beverage is prepared by com- bining 1 part concentrate with 5 parts water. In certain exemplary embodiments the additional water used to form the full strength beverages is carbonated water. In certain other embodiments, a full strength beverage is directly prepared without the formation of a concentrate and subsequent dilution.

Water is a basic ingredient in the beverages disclosed here, typically being the vehicle or primary liquid portion in which the remaining ingredients are dissolved, emulsified, suspended or dispersed. Purified water can be used in the manufacture of certain embodiments of the beverages disclosed here, and water of a standard beverage quality can be employed in order not to adversely affect beverage taste, odor, or appearance. The water typically will be clear, colorless, free from objectionable minerals, tastes and odors, free from organic matter, low in alkalinity and of acceptable microbiological quality based on industry and government standards applicable at the time of producing the beverage. In certain typical embodiments, water is present at a level of from about 80% to about 99.9% by weight of the beverage. In at least certain exemplary embodiments the water used in beverages and concentrates disclosed here is "treated water," which refers to water that has been treated to reduce the total dissolved solids of the water prior to optional supplementation, e.g., with calcium as disclosed in U.S. Pat. No. 7,052,725. Methods of producing treated water are known to those of ordinary skill in the art and include deionization, distillation, filtration and reverse osmosis ("r-o"), among others. The terms "treated water," "purified water,", "demineralized water," "distilled water," and "r-o water" are understood to be generally synonymous in this discussion, referring to water from which substantially all mineral content has been removed, typically containing no more than about 500 ppm total dissolved solids, e.g. 250 ppm total dissolved solids.

In certain embodiments, colors derived from natural sources may be used as the only source of added colorant in beverage compositions, thereby avoiding the use of synthetic compounds to provide a desired color to the composition. In certain embodiments, the synthetic equivalents of one or more colors derived from natural sources are used as the only sources of added colorant in beverage compositions. In alternate embodiments, colors derived from natural sources, or their synthetic equivalents, may be employed in combination with synthetic colors. According to certain embodiments of the beverage products disclosed here, the colors derived from natural sources comprise one or more colors each derived from natural sources. As used herein, the term "colors derived from natural sources" includes any and all extracted products from one or more pigmented biological materials. In certain exemplary embodiments, the biological materials comprise plant materials. The coloring provided by colors derived from natural sources may be due to the presence of flavonoid compounds, such as anthocyanin compounds. Non-limiting examples of colors derived from natural sources comprising anthocyanins include purple sweet potato color, black carrot color, purple carrot color, black currant color and blueberry color. Alternatively, pigmentation can be provided by various other natural compounds, for example cyclohexene dione dimers such as carthamus yellow color, colors derived from the reaction of an iridoid and amino acids, such as found in gardenia blue color. As used herein, "synthetic equivalents" includes any and all synthetically manufactured compounds having the same structure as a color derived from a natural source.

The beverages may contain added anthocyanin as a colorant. As disclosed above, anthocyanins are a class of compounds that may provide pigmentation to colors derived from natural sources. For example, anthocyanins found in black currants (*Ribes nigrum*) that provide pigmentation include 3-diglucoside and 3-rutinoside of cyanidin and delphinidin. Similarly, blueberries (*Vaccinium augustifolium* or *Vaccinium corymbosum*) typically contain the following anthocyanins that provide pigmentation: 3-glucosides, 3-galactosides, and 3-arabinosides of cyanidin, delphinidin, peonidin, petunidin, and malvidin.

A blue color derived from natural sources is gardenia blue, which may be formed by the reaction of an iridoid and an amino acid. For example, hydrolysis of the iridoid glycoside geniposide with beta-glucosidase, as indicated below, produces the iridoid genipin. Amino acids, such as glycine, lysine or phenylalanine, will react with the colorless genipin and form blue pigments.

R = Glucose 1 (geniposide)
H 2 (genipin)

Geniposide $\xrightarrow{\text{Glucosidase}}$ Genipin $\xrightarrow{\text{Amino acid}}$ Blue pigments Further examples of colors derived from natural sources are *carthamus* yellow and *carthamus* red. *Carthamus* yellow and *carthamus* red may be derived from safflower (*Carthamus tinctorius*), and include cyclohexene dione dimers, which are classified as chalcone compounds. The chemical structure of *carthamus* yellow, or carthamin, is provided below.

Carthamin

Acid used in beverages disclosed here can serve any one or more of several functions, including, for example, providing antioxidant activity, lending tartness to the taste of the beverage, enhancing palatability, increasing thirst quenching effect, modifying sweetness and acting as a mild preservative by providing microbiological stability. Ascorbic acid, commonly referred to as "vitamin C", is often employed as an acidulant in beverages to also provide a vitamin to the consumer. Fumaric acid, maleic acid, mesaconic acid, itaconic acid and/or aconitic acid may be used alone or in combination with at least one other edible acid in a beverage composition to provide fading inhibition of colors derived from natural sources, as well as to serve any of the other purposes of acids in beverages discussed above. In certain embodiments, between about 30 ppm and 1000 ppm of an unsaturated dicarboxylic acid may be incorporated into a beverage composition to inhibit fading of colors derived from natural sources. In certain embodiments of the invention, the effective amount of one or more unsaturated dicarboxylic acids may be determined either qualitatively or quantitatively. For example, the effective amount may be an amount of unsaturated dicarboxylic acid that inhibits color fading such that any change in color is not readily noticeable to the human eye. Alternatively, the effective amount may be defined quantitatively as the amount of unsaturated dicarboxylic acid that prevents the absorbance of a beverage composition at its optimal wavelength measured using a spectrophotometer from decreasing more than a particular magnitude, such as 25% of the initial absorbance of the composition at its maximum wavelength.

In an embodiment of the invention, fumaric acid may be provided by an acid blend of fumaric acid, malic acid and tartaric acid, which can be commercially obtained as Fruitaric® acid, such as the Fruitaric® acid manufactured by Isegen South Africa (Pty) Ltd, Isipingo, Durban, South Africa. In certain exemplary embodiments, maleic anhydride may be added to a beverage composition with an acid, and over time the maleic anhydride will undergo hydrolysis to form maleic acid within the beverage. Any suitable edible acid may be used to hydrolyze the maleic anhydride, for example citric acid, malic acid, tartaric acid, phosphoric acid, ascorbic acid, lactic acid, formic acid, fumaric acid, gluconic acid, succinic acid and/or adipic acid.

The acid can be used in solution form, for example, and in an amount sufficient to provide the desired pH of the beverage. Typically, for example, the one or more acids of the acidulant are used in amount, collectively, of from about 0.01% to about 1.0% by weight of the beverage, e.g., from about 0.05% to about 0.5% by weight of the beverage, such as 0.1% to 0.25% by weight of the beverage, depending upon the acidulant used, desired pH, other ingredients used, etc. In certain embodiments of the invention, all of the acid included in a beverage composition may be provided by one or more alpha,beta-unsaturated dicarboxylic acids.

The pH of at least certain exemplary embodiments of the beverages disclosed here can be a value within the range of 2.5 to 7.0. The acid in certain exemplary embodiments can enhance beverage flavor. Too much acid can impair the beverage flavor and result in sourness or other off-taste, while too little acid can make the beverage taste flat and reduce microbiological safety of the product. It will be within the ability of those skilled in the art, given the benefit of this disclosure, to select a suitable acid or combination of acids and the amounts of such acids for the acidulant component of any particular embodiment of the beverage products disclosed here.

Sweeteners suitable for use in various embodiments of the beverages disclosed here include nutritive and non-nutritive, natural and artificial or synthetic sweeteners. Suitable non-nutritive sweeteners and combinations of sweeteners are selected for the desired nutritional characteristics, taste profile for the beverage, mouthfeel and other organoleptic factors. Non-nutritive sweeteners suitable for at least certain exemplary embodiments include, but are not limited to, for example, peptide based sweeteners, e.g., aspartame, neotame, and alitame, and non-peptide based sweeteners, for example, sodium saccharin, calcium saccharin, acesulfame potassium, sodium cyclamate, calcium cyclamate, neohesperidin dihydrochalcone, and sucralose. In certain embodiments the sweetener comprises acesulfame potassium. Other non-nutritive sweeteners suitable for at least certain exemplary embodiments include, for example, sorbitol, mannitol, xylitol, glycyrrhizin, D-tagatose, erythritol, meso-erythritol, maltitol, maltose, lactose, fructo-oligosaccharides, Lo Han Guo powder, xylose, arabinose, isomalt, lactitol, maltitol, trehalose, and ribose, and protein sweeteners such as thaumatin, monellin, brazzein, L-alanine and glycine, related compounds, and mixtures of any of them. Lo Han Guo, rebaudioside A, and monatin and related compounds are natural non-nutritive potent sweeteners. Suitable sweeteners also include rhamnose and sweetener fractions of stevia.

In at least certain exemplary embodiments of the beverages disclosed here, the sweetener component can include nutritive, natural crystalline or liquid sweeteners such as sucrose, liquid sucrose, fructose, liquid fructose, glucose, liquid glucose, glucose-fructose syrup from natural sources such as apple, chicory, honey, etc., e.g., high fructose corn syrup, invert sugar, maple syrup, maple sugar, honey, brown sugar molasses, e.g., cane molasses, such as first molasses, second molasses, blackstrap molasses, and sugar beet molasses, sorghum syrup, Lo Han Guo juice concentrate, agave and/or others. Such sweeteners are present in at least certain exemplary embodiments in an amount of from about 0.1% to about 20% by weight of the beverage, such as from about 6% to about 16% by weight, depending upon the desired level of sweetness for the beverage. To achieve desired beverage uniformity, texture and taste, in certain exemplary embodiments of the natural beverage products disclosed here, standardized liquid sugars as are commonly employed in the beverage industry can be used. Typically such standardized sweeteners are free of traces of nonsugar solids which could adversely affect the flavor, color or consistency of the beverage.

Non-nutritive, high potency sweeteners typically are employed at a level of milligrams per fluid ounce of beverage, according to their sweetening power, any applicable regulatory provisions of the country where the beverage is to be marketed, the desired level of sweetness of the beverage, etc. It will be within the ability of those skilled in the art, given the benefit of this disclosure, to select suitable additional or alternative sweeteners for use in various embodiments of the beverage products disclosed here.

Preservatives may be used in certain embodiments of the beverages disclosed here. That is, certain exemplary embodiments contain an optional dissolved preservative system. Solutions with a pH below 4 and especially those below 3 typically are "microstable," i.e., they resist growth of microorganisms, and so are suitable for longer term storage prior to consumption without the need for further preservatives. However, an additional preservative system can be used if desired. If a preservative system is used, it can be added to the beverage product at any suitable time during production, e.g., in some cases prior to the addition of the sweetener. As used here, the terms "preservation system" or "preservatives" include all suitable preservatives approved for use in food and beverage compositions, including, without limitation, such known chemical preservatives as benzoic acid, benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), lauryl arginate ester, cinnamic acid, e.g., sodium and potassium cinnamates, polylysine, and antimicrobial essential oils, dimethyl dicarbonate, and mixtures thereof, and antioxidants such as ascorbic acid, EDTA, BHA, BHT, TBHQ, EMIQ, dehydroacetic acid, ethoxyquin, heptylparaben, and combinations thereof.

Preservatives can be used in amounts not exceeding mandated maximum levels under applicable laws and regulations. The level of preservative used typically is adjusted according to the planned final product pH, as well as an evaluation of the microbiological spoilage potential of the particular beverage formulation. The maximum level employed typically is about 0.05% by weight of the beverage. It will be within the ability of those skilled in the art, given the benefit of this disclosure, to select a suitable preservative or combination of preservatives for beverages according to this disclosure. In certain embodiments of the invention, benzoic acid or its salts (benzoates) may be employed as preservatives in the beverage products.

Other methods of beverage preservation suitable for at least certain exemplary embodiments of the beverage products disclosed here include, e.g., aseptic packaging and/or heat treatment or thermal processing steps, such as hot filling, tunnel pasteurization, and non-thermal processing. Such steps can be used to reduce yeast, mold and microbial growth in the beverage products. For example, U.S. Pat. No. 4,830,862 to Braun et al. discloses the use of pasteurization in the production of fruit juice beverages as well as the use of suitable preservatives in carbonated beverages. U.S. Pat. No. 4,925,686 to Kastin discloses a heat-pasteurized freezable fruit juice composition which contains sodium benzoate and potassium sorbate. In general, heat treatment includes hot fill methods typically using high temperatures for a short time, e.g., about 190° F. for 10 seconds, tunnel pasteurization methods typically using lower temperatures for a longer time, e.g., about 160° F. for 10-15 minutes, and retort methods typically using, e.g., about 250° F. for 3-5 minutes at elevated pressure, i.e., at pressure above 1 atmosphere.

The beverage products disclosed here optionally contain a flavor composition, for example, natural and synthetic fruit flavors, botanical flavors, other flavors, and mixtures thereof. As used here, the term "fruit flavor" refers generally to those flavors derived from the edible reproductive part of a seed plant. Included are both those wherein a sweet pulp is associated with the seed, e.g., banana, tomato, cranberry and the like, and those having a small, fleshy berry. The term berry also is used here to include aggregate fruits, i.e., not "true" berries, but that are commonly accepted as a berry. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime and grapefruit, and such flavors as apple, pomegranate, grape, cherry, and pineapple flavors and the like, and mixtures thereof. In certain exemplary embodiments the beverage concentrates and beverages comprise a fruit flavor component, e.g., a juice concentrate or juice. As used here, the term "botanical flavor" refers to flavors derived from parts of a plant other than the fruit. As such, botanical flavors can include those flavors derived from essential oils and extracts of nuts, bark, roots and leaves. Also included within the term "botanical flavor" are synthetically prepared flavors made to simulate botanical flavors derived from natural sources. Examples of such flavors include cola flavors, tea flavors, and the like, and mixtures thereof. The flavor component can further comprise a blend of the above-mentioned flavors. The particular amount of the flavor component useful for imparting flavor characteristics to the beverages of the present invention will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Juices suitable for use in at least certain exemplary embodiments of the beverage products disclosed here include, e.g., fruit, vegetable and berry juices. Juices can be employed in the present invention in the form of a concentrate, puree, single-strength juice, or other suitable forms. The term "juice" as used here includes single-strength fruit, berry, or vegetable juice, as well as concentrates, purees, milks, and other forms. Multiple different fruit, vegetable and/or berry juices can be combined, optionally along with other flavorings, to generate a beverage having the desired flavor. Examples of suitable juice sources include plum, prune, date, currant, fig, grape, red grape, sweet potato, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, lychee, lemon, orange, lime, tangerine, mandarin orange, tangelo, and pomelo and grapefruit, etc. Numerous additional and alternative juices suitable for use in at least certain exemplary embodiments will be apparent to those skilled in the art given the benefit of this disclosure. In the beverages of the present invention employing juice, juice may be used, for example, at a level of at least about 0.2% by weight of the beverage. In certain exemplary embodiments juice is employed at a level of from about 0.2% to about 40% by weight of the beverage. Typically, juice can be used, if at all, in an amount of from about 1% to about 20% by weight.

Other flavorings suitable for use in at least certain exemplary embodiments of the beverage products disclosed here include, e.g., spice flavorings, such as *cassia*, clove, cinnamon, pepper, ginger, vanilla spice flavorings, cardamom, coriander, root beer, sassafras, ginseng, and others. Numerous additional and alternative flavorings suitable for use in at least certain exemplary embodiments will be apparent to those skilled in the art given the benefit of this disclosure. Flavorings can be in the form of an extract, oleoresin, juice concentrate, bottler's base, or other forms known in the art. In at least certain exemplary embodiments, such spice or other flavors complement that of a juice or juice combination.

The one or more flavorings can be used in the form of an emulsion. A flavoring emulsion can be prepared by mixing some or all of the flavorings together, optionally together with other ingredients of the beverage, and an emulsifying agent. The emulsifying agent may be added with or after the flavorings mixed together. In certain exemplary embodiments the emulsifying agent is water-soluble. Exemplary suitable emulsifying agents include gum acacia, modified starch, carboxymethylcellulose, gum tragacanth, gum ghatti and other suitable gums. Additional suitable emulsifying agents will be apparent to those skilled in the art of beverage formulations, given the benefit of this disclosure. The emulsifier in exemplary embodiments comprises greater than about 3% of the mixture of flavorings and emulsifier. In certain exemplary embodiments the emulsifier is from about 5% to about 30% of the mixture.

Carbon dioxide can be used to provide effervescence to certain exemplary embodiments of the beverages disclosed here. Any of the techniques and carbonating equipment known in the art for carbonating beverages can be employed. Carbon dioxide can enhance the beverage taste and appearance and can aid in safeguarding the beverage purity by inhibiting and destroying objectionable bacteria. In certain embodiments, for example, the beverage has a $CO_2$ level up to about 7.0 volumes carbon dioxide. Typical embodiments may have, for example, from about 0.5 to 5.0 volumes of carbon dioxide. As used here and independent claims, one volume of carbon dioxide is defined as the amount of carbon dioxide absorbed by any given quantity of water at 60° F. (16° C.) temperature and atmospheric pressure. A volume of gas occupies the same space as does the water by which it is absorbed. The carbon dioxide content can be selected by those skilled in the art based on the desired level of effervescence and the impact of the carbon dioxide on the taste or mouthfeel of the beverage. The carbonation can be natural or synthetic.

The beverage concentrates and beverages disclosed here may contain additional ingredients, including, generally, any of those typically found in beverage formulations. These additional ingredients, for example, can typically be added to a stabilized beverage concentrate. Examples of such additional ingredients include, but are not limited to, caffeine, caramel and other coloring agents or dyes, antifoaming agents, gums, emulsifiers, tea solids, phytochemicals, cloud components, and mineral and non-mineral nutritional supplements. Examples of non-mineral nutritional supplement ingredients are known to those of ordinary skill in the art and include, for example, antioxidants and vitamins, including Vitamins A, D, E (tocopherol), C (ascorbic acid), $B_1$ (thiamine), $B_2$ (riboflavin), $B_3$ (nicotinamide), $B_4$ (adenine), $B_5$ (pantothenic acid, calcium), $B_6$ (pyridoxine HCl), $B_{12}$ (cyanocobalamin), and $K_1$ (phylloquinone), niacin, folic acid, biotin, and combinations thereof. The optional non-mineral nutritional supplements are typically present in amounts generally accepted under good manufacturing practices. Exemplary amounts are between about 1% and about 100% RDV, where such RDV are established. In certain exemplary embodiments the non-mineral nutritional supplement ingredient(s) are present in an amount of from about 5% to about 20% RDV, where established.

In some embodiments, caffeine may be added. The caffeine may be added in any suitable format; for example as an artificial caffeine, or a natural sourced caffeine such like extracted from botanicals such as coffee, Guarana, tea, etc.

REFERENCES

Technical Standards for Testing & Assessment of Health Food (Version 2003), proposed by Ministry of Health
Xue-Ling Zhang, etc., Anti-Fatigue Activity of Extracts of Stem Bark from *Acanthopanax senticosus*, Molecules, 2011, 16, 28~37
J. L. Wu, etc., Effects of L-Malate on Physical Stamina and Activities of Enzymes Related to the Malate-Aspartate Shuttle in Liver of Mice, Physiological Research, 2007, 56:213~220,
T. Moriura, H. Matsuda, M. Kubo, Pharmacological study on *Agkistrodon blomhoffii* blomhoffii BOIE. V. anti-fatigue effect of the 50% ethanol extract in acute weight-loaded forced swimmingtreated rats, Biol. Pharm. Bull. 19 (1996) 62-66.
Jin Zhenjun, Zhang Xiaowen, Equi-Probability Sum Curves and Q50—the new method in effect estimating of therapy combination[J], The Journal of Shanghai Second Medical College; 1981, 15-18
Jin Zhenjun, addition in drug combination, Zhongguo Yao Li Xue Bao, 1980, 1:70~76
Jia Rao etc., Curcumin reduces expression of Bcl-2, leading to apoptosis in daunorubicin-insensitive CD34+ acute myeloid leukemia cell lines and primary sorted CD34+ acute myeloid leukemia cells, Journal Translation Medicine, 2011, 9:71

EXAMPLE 1

Beverage Preparation (Reduced Sugar Plus Stevia)
A beverage containing the herbal extract was prepared with the formulation in table 4:

TABLE 4

Beverage Ingredients.

| Ingredients | Weight (Kg) |
| --- | --- |
| Citric Acid | 4.008 |
| Sodium Citrate | 0.681 |
| Vitamin C | 0.681 |
| *Stevia* | 0.102 |
| Colorants | 0.920 |
| Flavorant | 6.132 |
| Herbal Extracts | 15.500 |
| Sucrose | 238.476 |
| Water | 3235.610 |

The beverage product was made using the following protocol. 180.00 Kg deionized water was introduced into a sugar dissolving tank, heated to 70~80° C., and agitated. 238.48 Kg sucrose were added and dissolved by agitation to create a syrup. Brix was then adjusted to 50% to 60%.

The syrup was filtered through a 30 mm mesh and transferred to a mixing tank with mild agitation. The syrup was then cooled and maintained at a temperature of less than 25 degrees. Water (1500.00 Kg) was added to the mixing tank at 15-30° C., with agitation.

Deionized Water (200.00 Kg) water at 25-35° C. was added to a pre-dissolving tank and agitated. Herbal extracts (15.50 Kg; prepared as in Example 8) were added into the pre-dissolving tank and agitated until dissolved to prepare an herbal concentrate, which was added to the mixing tank.

Next, deionized water (100.00 Kg) at 15-30° C. was added into a second pre-dissolving tank and agitated. Citric acid (4.09 Kg), sodium citrate (0.68 Kg), vitamin C (0.68 Kg) into the pre-dissolving tank and agitated until dissolved, then transferred into the mixing tank.

A stevia solution was prepared by dissolving 0.10 Kg stevia in 100.00 Kg deionized water at 15-30° C. The stevia solution was added to the mixing tank.

Colorants (0.92 Kg), flavor (6.13 Kg) were added, along with an additional 1155.61 Kg deionized water at 15-30° C., into the mixing tank. The combined ingredients were mixed until homogeneous and tested to ensure the Brix, Total Acid, pH were with an acceptable range. The solution was then filtered through a 100 size mesh, sterilized, filled, cooled and packed.

EXAMPLE 2

Beverage Preparation (Full Sugar)
A beverage containing the herbal extract was prepared according to the formulation given in table 5:

TABLE 5

Beverage containing herbal extract

| Ingredients | Weight (Kg) |
| --- | --- |
| Citric Acid | 4.429 |
| Sodium Citrate | 0.341 |
| Vitamin C | 0.681 |
| Colorants | 0.920 |
| Flavor | 3.407 |
| Herbal Extracts | 15.500 |
| Sucrose | 306.612 |
| Water | 3197.550 |

The beverage product was made using the following protocol. 250.00 Kg deionized water was introduced into a sugar dissolving tank, heated to 70~80 degrees, and agitated.

306.61 Kg sucrose were added and dissolved by agitation to create a syrup. Brix was then adjusted to 50% to 60%.

The syrup was filtered through a 30 mm mesh and transferred to a mixing tank with mild agitation. The syrup was then cooled and maintained at a temperature of less than 25 degrees. Water (1500.00 Kg) was added to the mixing tank at 15-30° C., with agitation.

Deionized Water (200.00 Kg) water at 25-35° C. was added to a pre-dissolving tank and agitated. Herbal extracts (15.50 Kg; prepared as in Example 8) were added into the pre-dissolving tank and agitated until dissolved to prepare an herbal concentrate, which was added to the mixing tank.

Next, deionized water (100.00 Kg) at 15-30° C. was added into a second pre-dissolving tank and agitated. Citric acid (4.43 Kg), sodium citrate (0.34 Kg), vitamin C (0.68 Kg) into the pre-dissolving tank and agitated until dissolved, then transferred into the mixing tank.

Colorants (0.92 Kg), flavorant (3.41 Kg) were added into the mixing tank, along with an additional 1147.55 Kg deionized water at 15-30° C. into mixing tank. The combined ingredients were mixed until homogeneous and tested to ensure the Brix, Total Acid, pH were with an acceptable range. The solution was then filtered through a 100 size mesh, sterilized, filled, cooled and packed

EXAMPLE 3

Effect of Extract on Physical Fatigue; Burden Swimming

The effect of herbal extract on relieving physical fatigue was examined under a protocol approved by the China MOH for assessing relief of physical fatigue, including measurement of the time-to-exhaustion of mice during burden swimming, measurement of the blood lactic acid, serum urea and glycogen.

Forty male mice were randomly separated into 4 groups of 10: control group, Group L (Low), Group M (Medium), and Group H (High). Groups L, M, and H were fed with the herb extract for 30 days. The chemical contents of herbs provided to each Group (calculated as human dose) are listed in table 6.

TABLE 6

Amounts of Ingredient in servings for Groups L, M, and H

| | Dose (mg/60 Kg/day) | | |
|---|---|---|---|
| Ingredients | Low | Medium | High |
| Saponins (calculated as ginsengoside Re) | 3.9 | 7.9 | 15.9 |
| Flavonoids (calculated as rutin) | 18.9 | 37.9 | 75.6 |
| Polysaccharides | 50.2 | 100.5 | 201.0 |
| Total Free Amino Acid | 3.9 | 7.8 | 15.6 |

Figure 1:
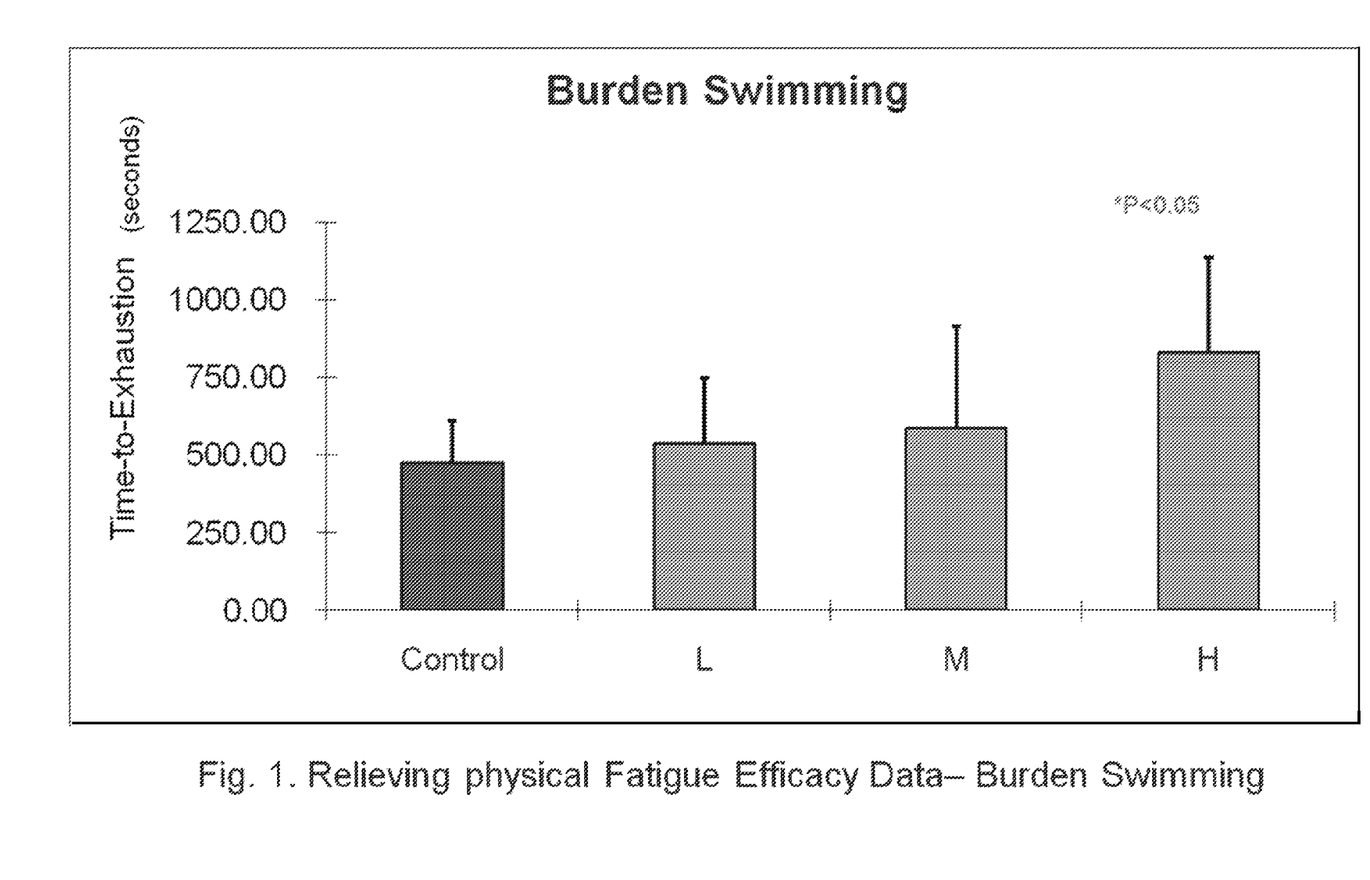
FIG. 1 illustrates the ability of an herbal extract to enhance time-to-exhaustion in a mice burden swimming test. The mice were fed with low (L), medium (M) and high (H) doses of the herbal extract as described in Example 3. The high dose showed a significant difference of $P<0.05$ compared to control.

To test stamina, the time-to-exhaustion of burden swimming was tested. Time-to-exhaustion provides an objective indication of stamina and is useful in determining whether the extracts alleviate fatigue. 30 minutes after the final feed, a lead sheet (5% of mouse body weight) was attached to the tails. The mice were introduced to a pool (water temp; 25° C.) and time-to-exhaustion, from start to an inability to swim, was measured. Compared with control group, the time-to-exhaustion of the group L, M, H are longer. Group H is significant longer (P value less than 0.05). The testing results are listed in table 7 and presented graphically in FIG. 1.

TABLE 7

Time-to-exhaustion data for mice with or without herbal extract consumption

| Groups | Number of Mice in Group | Time-to-Exhaustion (seconds) |
|---|---|---|
| Control | 10 | 475.3 ± 135.2 |
| Group L | 10 | 536.2 ± 211.7 |
| Group M | 10 | 587.7 ± 327.9 |
| Group H | 10 | 831.4 ± 304.5 |

EXAMPLE 4

Effect of Extract on Physical Fatigue; Blood Lactic Acid

Figure 2:
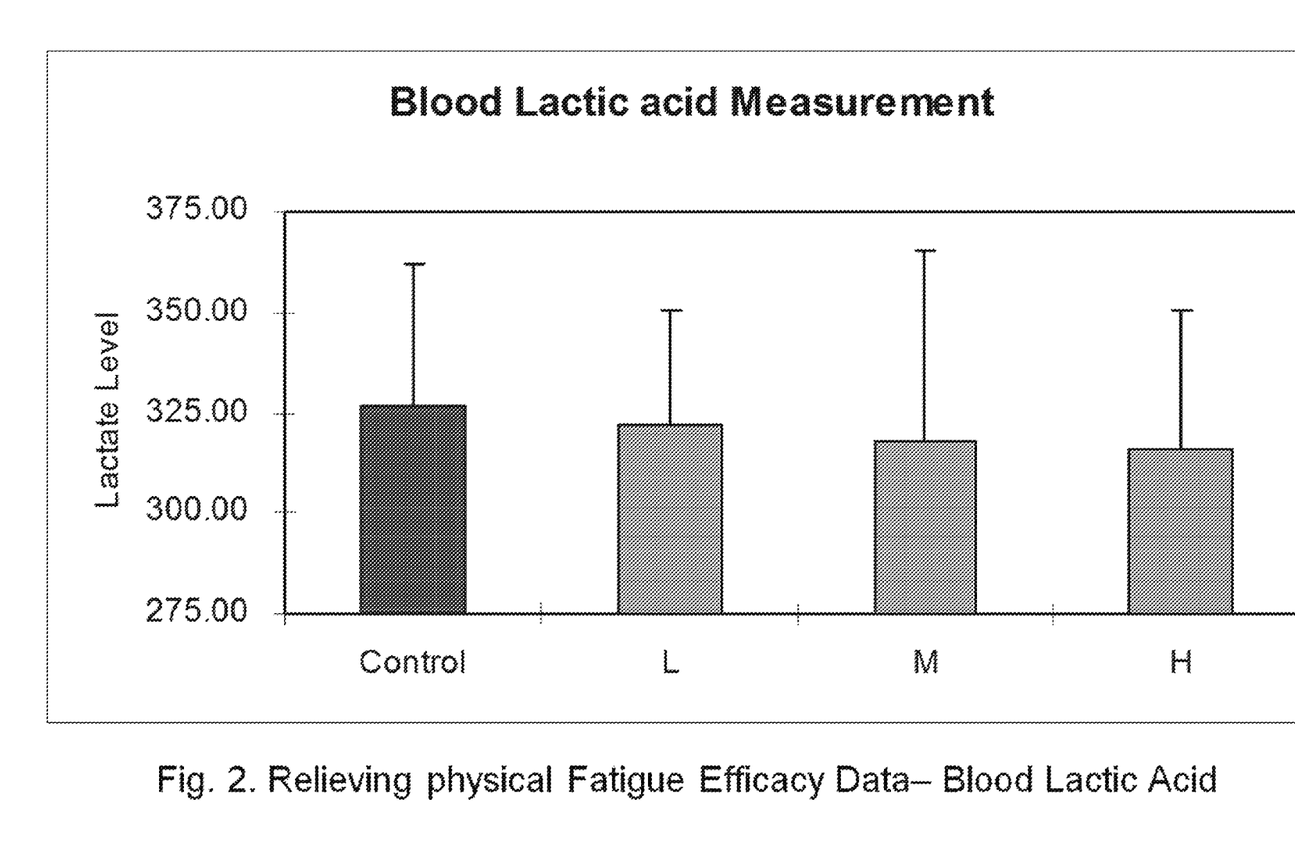
FIG. 2 illustrates blood lactic acid (area under the curve) in mice fed with low (L), medium (M), and high (H) doses of the herbal extract is shown. See Example 4.

Mice were prepared as described in Example 3. 30 minutes after the last feeding, a first blood sample was taken. The mice were then introduced into a swimming pool without burden (water temp. 30° C.) for 10 minutes. A second sample was taken after the swim. A third blood sample was taken after a further 20 minute break. The blood lactic acid level in groups L, M, H were each lower than the control group. The testing results are listed in table 8 and presented graphically in FIG. 2:

TABLE 8

Blood lactic acid in mice with or without herbal administered

| Groups | Number of Mice in Group | Blood Lactic Acid (Area Under the Curve) |
|---|---|---|
| Control | 10 | 326.6 ± 35.7 |
| Group L | 10 | 321.9 ± 28.8 |
| Group M | 10 | 317.8 ± 47.4 |
| Group H | 10 | 315.5 ± 35.0 |

EXAMPLE 5

Effect of Extract on Physical Fatigue; Serum Urea Data

Figure 3:
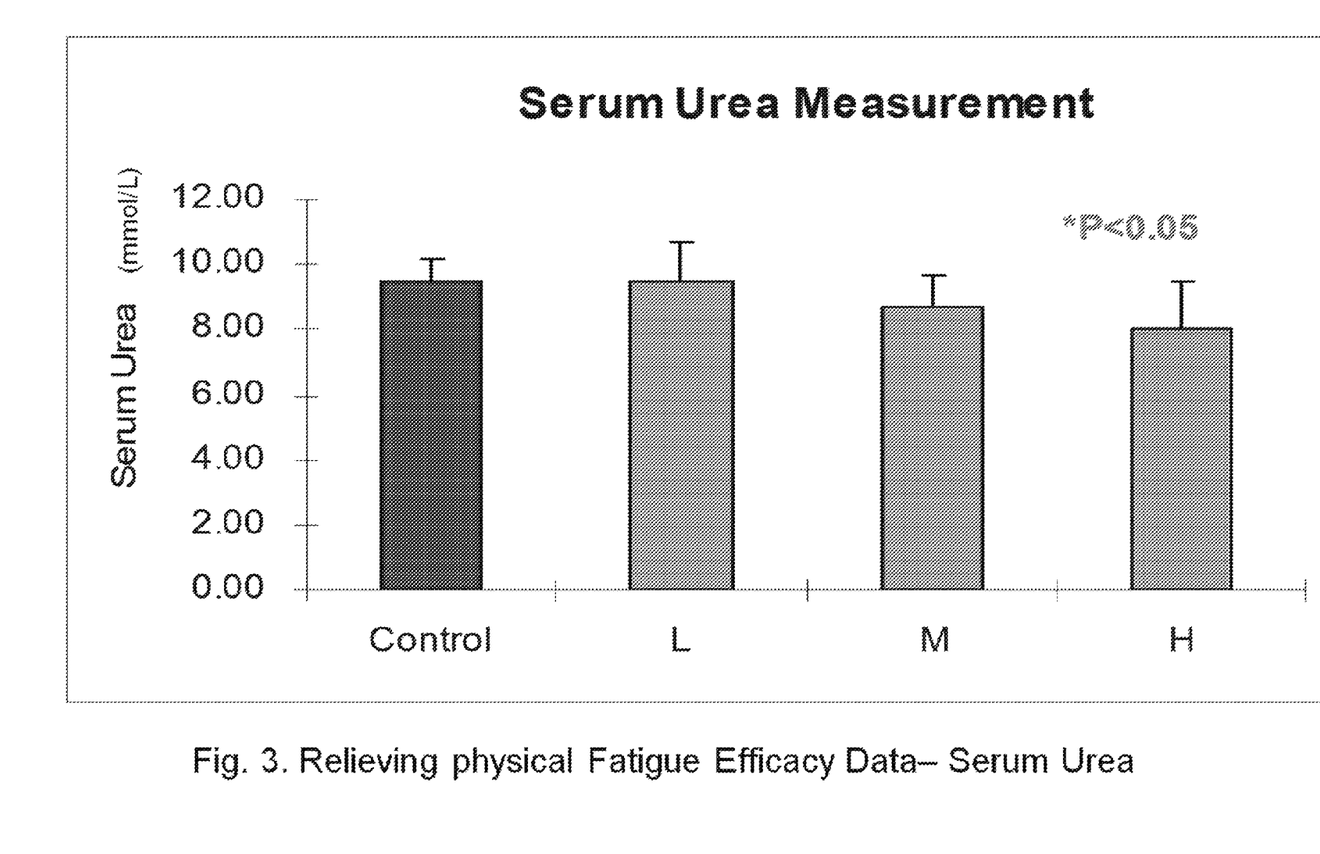
FIG. 3 illustrates serum urea (m mol/L) in mice fed with low (L), medium (M), and high (H) doses of the herbal extract is shown. See Example 5.

Mice were prepared as described in Example 3. 30 minutes after last feeding, mice were sent for swimming without burden (water temp. 30° C.) for 90 minutes, then allowed to recover for 60 minutes before taking blood sample. Compared with control group, the serum urea levels in each of groups L, M, and H were lower. Group H is significant lower than control group, and the P value is less than 0.05. The test results are listed in table 9 and represented graphically in FIG. 3.

TABLE 9

Serum urea in mice with or without herbal extract consumption.

| Groups | Number of Mice in Group | Serum Urea (mmol/L) |
|---|---|---|
| Control | 10 | 9.5 ± 0.7 |
| Group L | 10 | 9.5 ± 1.2 |
| Group M | 10 | 8.7 ± 1.0 |
| Group H | 10 | 8.0 ± 1.5 |

EXAMPLE 6

Effect of Extract on Physical Fatigue; Glycogen

Figure 4:
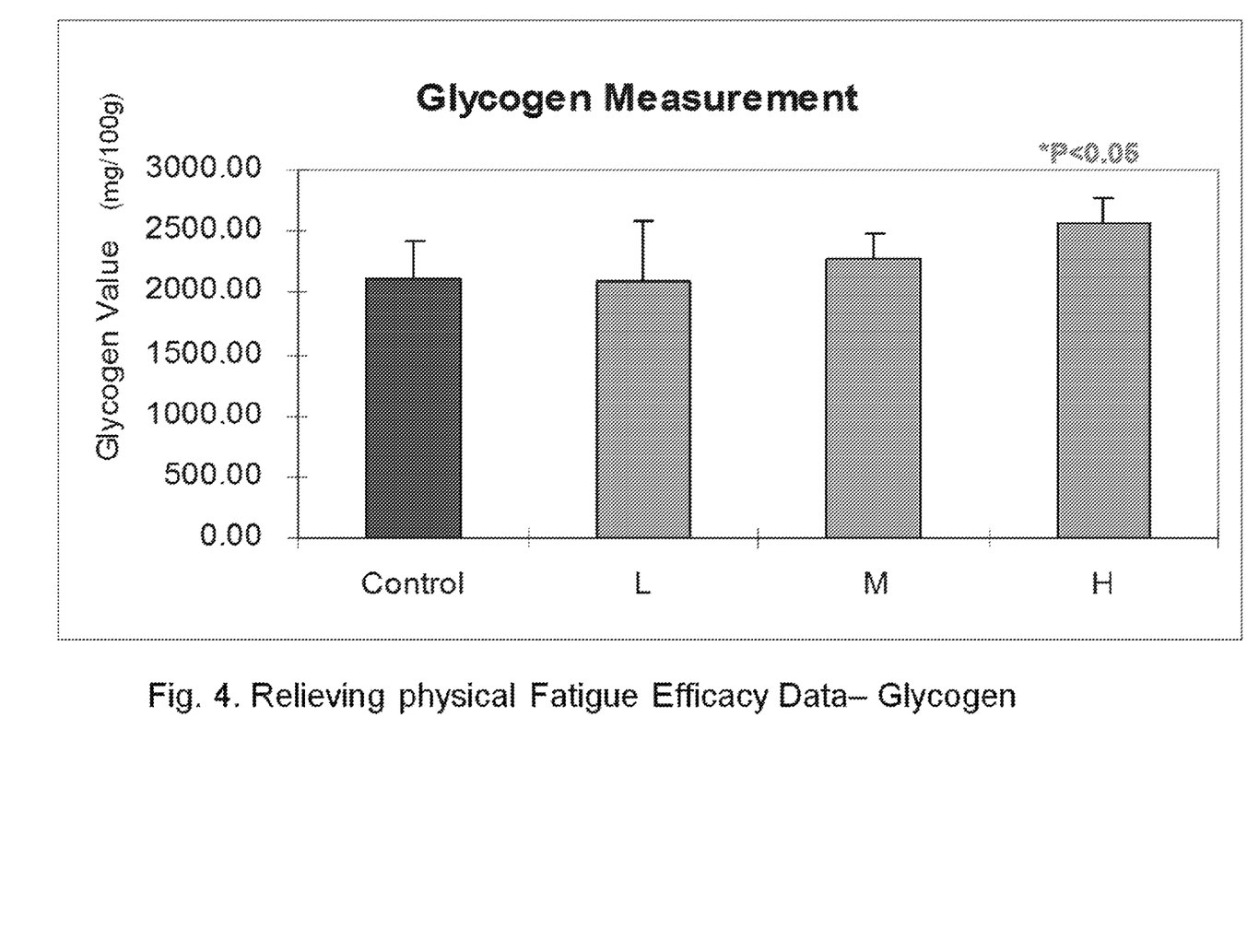
FIG. 4 illustrates glycogen (mg/100 g) in mice fed with low (L), medium (M), and high (H) doses of the herbal extract is shown. See Example 6.

Mice were prepared as described in Example 1. 30 minutes after last feeding, mice were sacrificed and their livers were tested for Glycogen content. Compared with control group, the glycogen levels of groups M and H are higher. Group H is significant higher than control group, and the P value is less than 0.05. The testing results are listed below in table 10 and represented graphically in FIG. 4.

TABLE 10

Glycogen levels in mice with or without the herbal extract administered

| Groups  | Number of Mice in Group | Glycogen (mg/100 g) |
|---------|-------------------------|---------------------|
| Control | 10                      | 2115.7 ± 297.5      |
| Group L | 10                      | 2093.2 ± 500.2      |
| Group M | 10                      | 2266.4 ± 216.0      |
| Group H | 10                      | 2570.7 ± 192.2      |

EXAMPLE 7

Consumer Perceived Energy Increase/Relief of Fatigue

A double-blind in-home usage placement study was conducted to assess perceived fatigue relief after consuming the beverage. The study was a sequential monadic test (i.e., each participant tests 2 products: beverage containing the herbal extract and a control caffeine-containing beverage.

The sequence of tasting each of the two products was randomized: after 3 days of in-home placement of the first product, the second product was given. The participants were selected according to the following criteria: 20-39 yrs old, even split of 20-29/30-39; equal numbers of males and female, 50% energy drink user, 50% energy drink non-users but with energy needs.

300 participants were randomly and equally divided into 4 groups and provided beverages as shown below. The information on the four groups is shown in table 11.

TABLE 11

Test Groups

| Group        | 1                | 2                | 3                | 4                |
|--------------|------------------|------------------|------------------|------------------|
| Participants | 75               | 75               | 75               | 75               |
| Test samples | 237 and Control  | 534 and Control  | 491 and Control  | 648 and Control  |

The control beverage "Caffeine Control" contained, per 250 ml, Brix 11.5, 125 mg taurine, 50 mg lysine, 50 mg inositol, 50 mg caffeine, 10 mg nicotinamide, 1 mg vitamin B6, and 3 µg vitamin B12. The contents of the test samples are listed in table 12. The contents for the herbal extract doses are listed in Table 6.

TABLE 12

Test Samples

| Code | Herbal extract dose (as in Table 6) | Guarana extract/ caffeine concentration | Sweetener          | Volume (ml) |
|------|-------------------------------------|-----------------------------------------|--------------------|-------------|
| 237  | Medium                              | No/0                                    | Sucrose & Stevia (Brix 7.5) | 200 |
| 534  | Medium                              | Yes/50 ppm                              | Glucose (Brix 12.8) | 200        |
| 491  | High                                | Yes/50 ppm                              | Glucose (Brix 13.2) | 200        |
| 648  | High                                | Yes/150 ppm                             | Glucose (Brix 13.3) | 200        |

Figure 5:
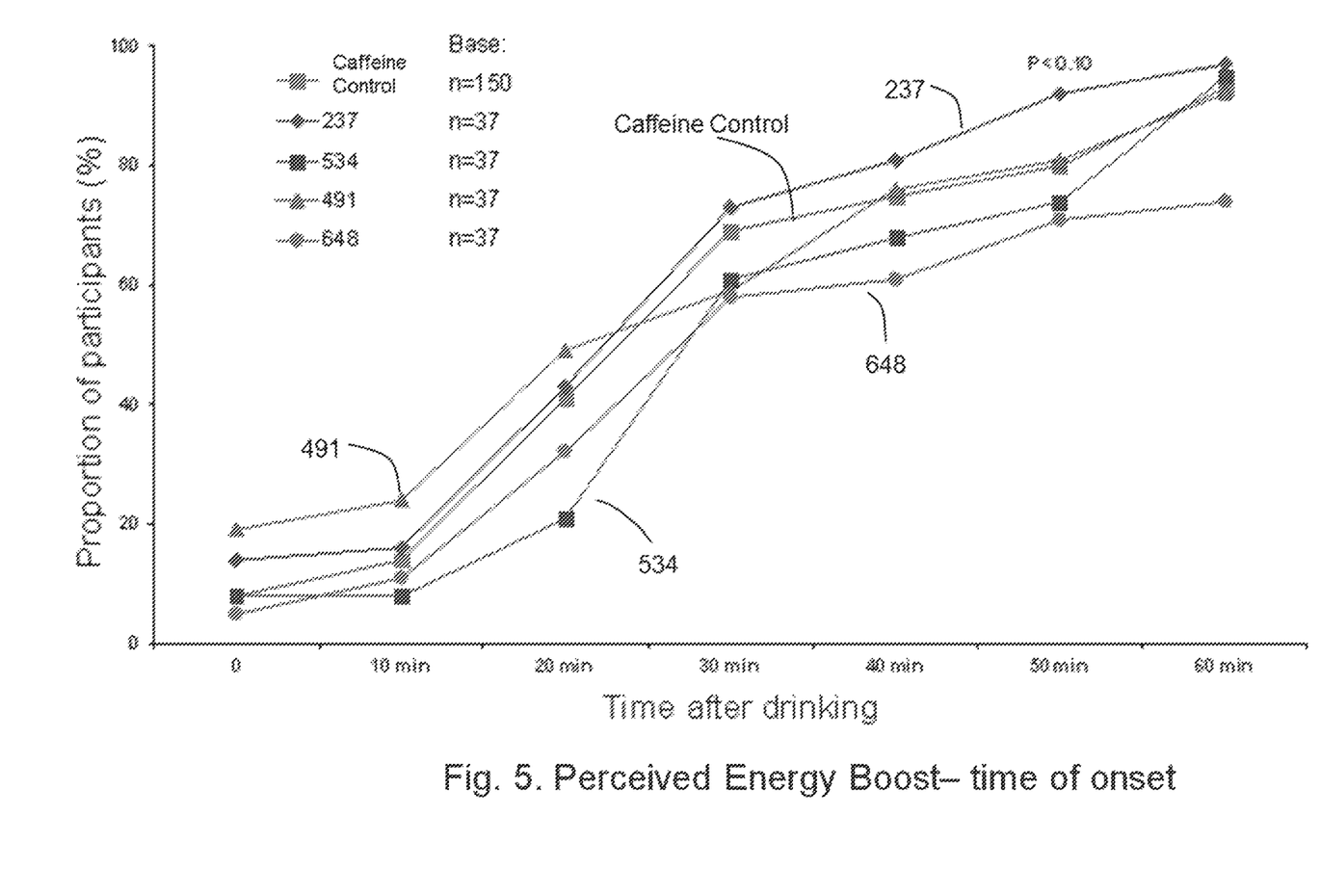
FIG. 5 illustrates the perceivable energy boosting benefit in a human consumer test. The indicated beverages were provided to test participants (See Example 7). The data shows the time after beverage consumption that participants perceived an increase in energy.

Participants were asked to identify when they perceived an increase in energy after consuming the beverage. As shown in FIG. 5, most test participants felt an increase in energy within an hour. Notably, testers who consumed the caffeine-free beverage 237 showed an earlier onset of the energy. In addition, more of the 237 testers identified a feeling of energy than the other beverages. Adding caffeine, in the form of a guarana extract, did not enhance either onset time or the proportion of testers who responded to the beverages. (Compare FIG. 7 "237" vs. "534").

Figure 6:
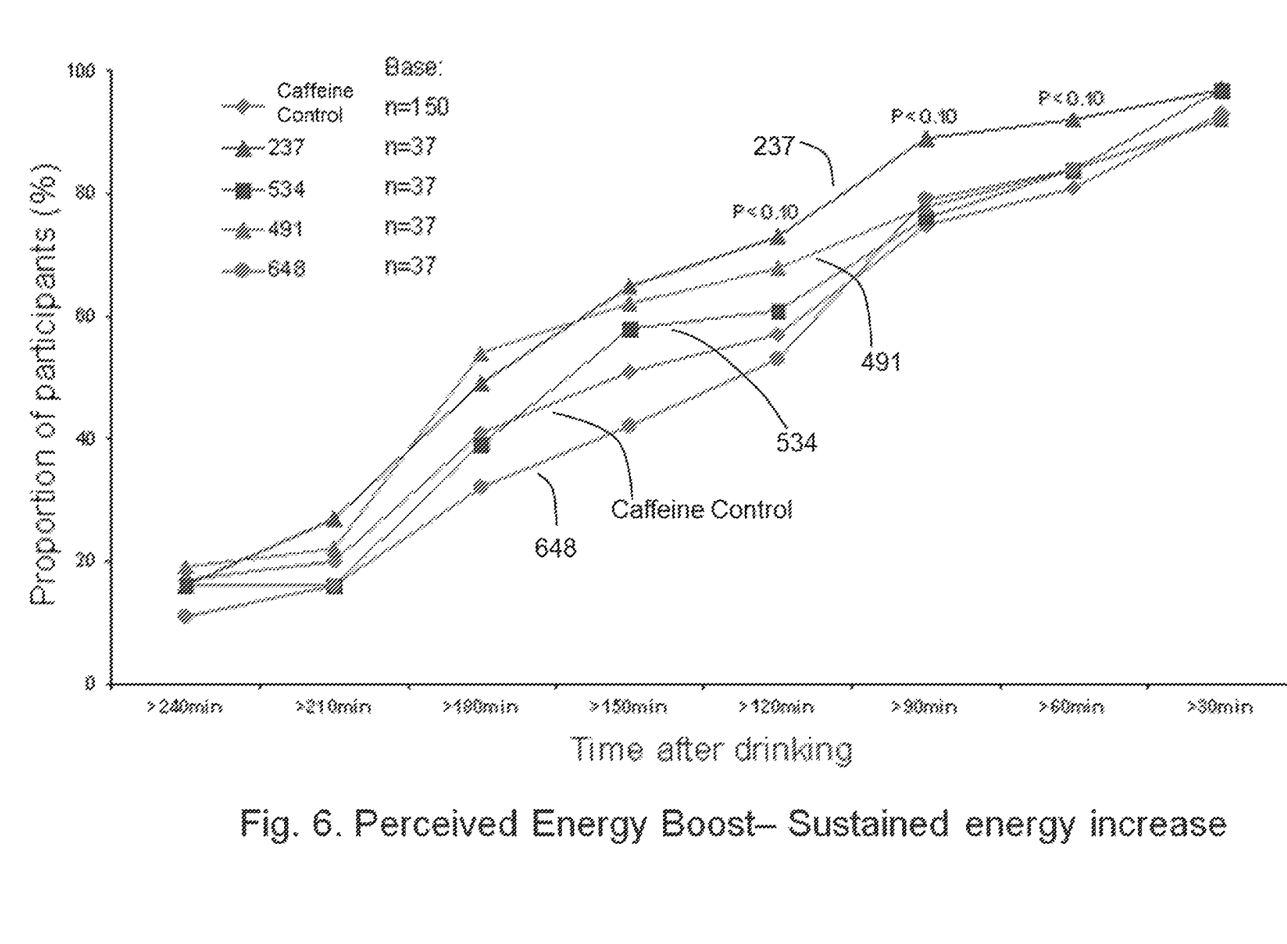
FIG. 6 illustrates the sustained effect of the energy boosting benefit in a human consumer test. The data shows the length of time after beverage consumption that participants still perceived the increased energy.

In addition, the 237 beverage provided a more sustained increase in energy perception compared to the other beverages. FIG. 6 shows the proportion of testers who continued to perceive the benefit after certain time periods. Testers who consumed beverage 237 showed substantially greater energy perception up to 2 hours after beverage consumption than the other beverages. See FIG. 6, "237" at 60 min, 90 min and 120 min after beverage consumption.

EXAMPLE 8

Preparing the Herbal Extract

An herbal extract was prepared as shown in FIG. 7. In a first step, 701, 200 Kg of herb materials were added to an extraction tank. The herb materials added were 71.4 Kg Duan-Geng-Wu-Jia leaves, 14.3 Kg Duan-Geng-Wu-Jia fruit, (A=85.7 i.e. 71.4+14.3); 57.1 Kg Gou-Qi-Zi (B=57.1) and 57.1 Kg Huang-Jing (C=57.1). Thus, B/C=1, and A/(B+C)=0.75, on a w/w/w basis.

A first extract was obtained by adding hot water (95° C.) to the herbs at a ratio of about 1:12 w/w. The water extract is removed from the extract tank after 45 minutes. In step 703, a second extract was performed using warm water (45° C.) at a ratio of 1:8 w/w. The first and second extracts were combined (Step 704) and treated to remove undesirable particulate matter was removed in step 705 in a three-part process using a filter screen, centrifugation and a pore membrane system The extracted liquid was concentrated in a two-step process using a membrane, followed by a vacuum concentrator. The concentrate was then blended with maltodextrin, sterilized using ultra-high temperature processing (step 709) and sprayed into a powder for further use or storage (step 710).

COMPARATIVE EXAMPLE 8

As an alternative to performing the extraction after combining each of the herb, parts, each herb part was separately extracted using the water temperatures and process described above, then the individual herb extract powders were combined.

What is claimed is:
1. An herbal extract composition comprising herbal extracts of Duan-Geng-Wu-Jia, Gou-Qi-Zi and Huang-Jing according to the following formulae:

$$\frac{1}{5} \leq \frac{B}{C} \leq 5,$$

and $$\frac{1}{5} \leq \frac{A}{B+C} \leq 5;$$

wherein A, B, and C are Duan-Geng-Wu-Jia, Gou-Qi-Zi, and Huang-Jing, respectively, and wherein the amounts of A, B, and C are w/w/w.

2. The composition of claim 1 wherein the formulae are:

$$\frac{2}{3} \leq \frac{B}{C} \leq \frac{3}{2},$$

and $$\frac{1}{3} \leq \frac{A}{B+C} \leq 1.$$

3. A beverage product comprising the herbal extract of claim 1.

4. The beverage product of claim 3 wherein the pH is 2.5 to 7.0.

5. The beverage product of claim 3 wherein the Brix is 0.2 to 18.0.

6. The beverage product of claim 3 further comprising a guarana extract.

7. The beverage product of claim 3 further comprising caffeine.

8. The beverage product of claim 3 wherein the beverage product is caffeine-free.

\* \* \* \* \*